(12) United States Patent
Martin et al.

(10) Patent No.: US 6,406,682 B1
(45) Date of Patent: Jun. 18, 2002

(54) SAXIFRAGA EXTRACTS FOR ARTIFICIALLY TANNING HUMAN SKIN

(75) Inventors: Richard Martin, Rochecorbon; Béatrice Belcour-Castro, La Riche; Cédric Galup, Levallois-Perret, all of (FR)

(73) Assignee: Societe L'Oreal, Paris (FR)

( * ) Notice: Subject to any disclaimer, the term of this patent is extended or adjusted under 35 U.S.C. 154(b) by 11 days.

(21) Appl. No.: 09/607,360

(22) Filed: Jun. 30, 2000

(30) Foreign Application Priority Data

Jul. 2, 1999 (FR) .............................. 99 08571

(51) Int. Cl.⁷ .............................. A61K 7/42; A61K 7/44; A61K 7/00; A61K 35/78
(52) U.S. Cl. .......................... 424/59; 424/60; 424/400; 424/401; 514/714
(58) Field of Search .................. 424/59, 60, 400, 424/401; 514/714

(56) References Cited

U.S. PATENT DOCUMENTS 6,153,208 A * 10/2000 McAtee et al. ............. 424/402
6,214,322 B1 * 4/2001 Castro et al. ................ 424/59

FOREIGN PATENT DOCUMENTS

| FR | 2409751 | 6/1979 |
| JP | 07069850 | 3/1995 |
| JP | 11092347 | 4/1999 |

OTHER PUBLICATIONS

STN, Serveur de Bases de Donnees, Karlsruhe, DE, Fichier Biosis, AN = 1997:170317, XP002134227.

STN, Serveur de Bases de Donnees, Karlsruhe, DE, Fichier CAPLUS, AN = 1971:01102, XP002134228.

* cited by examiner

Primary Examiner—Shelley A. Dodson
(74) Attorney, Agent, or Firm—Burns, Doane, Swecker & Mathis, L.L.P.

(57) ABSTRACT

Human skin is artificially tanned, darkened and/or browned by topically applying thereto, for such period of time as required to elicit the desired response, an effective self-tanning/coloring amount of at least one plant of the genus Saxifraga, advantageously in association with a thus-effective amount of another skin colorant, e.g., dihydroxyacetone ("DHA").

23 Claims, No Drawings

SAXIFRAGA EXTRACTS FOR ARTIFICIALLY TANNING HUMAN SKIN

CROSS-REFERENCE TO PRIORITY APPLICATION

This application claims priority under 35 U.S.C. §119 of FR-99/08571, filed Jul. 2, 1999, hereby expressly incorporated by reference.

BACKGROUND OF THE INVENTION

1. Technical Field of the Invention

The present invention relates to novel cosmetic/dermatological compositions comprising at least one extract of at least one plant from the genus Saxifraga, for the artificial tanning, browning and/or darkening of human skin, imparting thereto an artificial coloration closely resembling that of a natural tan, and to the use of such novel compositions for the cosmetic applications indicated above.

2. Description of the Prior Art

It is today increasingly important to have a healthy appearance, and tanned skin is always a sign of good health. However, a natural tan is not always desirable since it necessitates prolonged exposure to UV radiation, in particular to UV-A radiation which is liable to induce an adverse change in the skin, in particular in the case of sensitive skin or of skin which is continually exposed to solar radiation. It is thus desirable to provide an alternative to a natural tan, which is compatible with the requirements of such skin types.

Most of the cosmetic products intended for artificially tanning the skin are based on carbonyl compounds which, by interacting with the amino acids in the skin, permit the formation of colored species.

Thus, it is known to this art that dihydroxyacetone, or DHA, is a particularly advantageous substrate which is commonly employed in cosmetics as an artificial tanning agent for the skin; when applied to the skin, in particular to the face, it elicits a tanning or browning effect similar in appearance to that which may result from prolonged exposure to sunlight (natural tanning) or under a UV lamp.

Nonetheless, topical application of DHA may present certain drawbacks. Thus, DHA has an unfortunate tendency, which is more or less pronounced depending on the nature of the medium in which it is formulated, to degrade over time, this degradation generally being ultimately reflected by an undesirable yellowing of the compositions containing same. The effect of such a phenomenon is that the activity of DHA, and in particular its ability to color the skin, may be reduced at the point in time of application of these compositions onto the skin. Hence, the intensity of the coloration imparted to the skin may appear as still insufficient.

Another drawback of DHA is the slow speed at which the coloration develops: specifically, several hours are required (in general 3 to 5 hours) in order for the coloration to be revealed. Furthermore, the coloration produced on the skin by DHA is often considered as being too yellow by users.

There is thus an increasing demand for self-tanning products which act rapidly and provide a coloration which is closer to that of a natural tan.

With a view towards satisfying this need, it has been proposed to combine DHA with various products: thus, WO-95/15742 describes the combination of DHA with amino acids. However, the use of such combinations is highly impractical since it requires either a two-stage application or complex separate packagings. FR-2,726,761 describes the combination of DHA with lawsone and/or juglone: in this instance also, such combination is unsatisfactory, this time on account of the risks of sensitization provided thereby.

Thus, serious need continues to exist for novel products and novel compositions which can artificially impart to the skin a coloration closely approximating that of a natural tan in a simple, effective, rapid and risk-free manner.

SUMMARY OF THE INVENTION

It has now unexpectedly and surprisingly been determined that certain specific compounds impart to the skin a long-lasting artificial coloration closely resembling that of a natural tan, and this immediately after topically applying such compounds onto the skin.

Briefly, the present invention features novel cosmetic/dermatological compositions well suited for artificially tanning the skin, comprising, formulated into a physiologically acceptable support (vehicle, diluent or carrier), an effective self-tanning amount of at least one extract of at least one plant from the genus Saxifraga.

The present invention thus also features the use of at least one extract as described above in, or for the production of, compositions suited for artificially coloring the skin.

This invention also features a cosmetic regime/regimen for the skin to impart coloration thereto, comprising topically applying onto the skin an effective amount of an extract or of a cosmetic composition as described above.

The compositions and the applications thereof in accordance with the invention make it possible to obtain an artificial coloration close to that of a natural tan within an exceptionally short time period. Thus, an immediate coloration is obtained, which permits a visualization of the application and consequently better homogeneity in the spreading of the composition on the skin and thus the coloration resulting therefrom. Furthermore, the artificial coloration provided on the skin according to the invention is extremely close to that of a natural tan and also very resistant to water and to the environment/weather (it can persist on the skin for several days).

DETAILED DESCRIPTION OF BEST MODE AND SPECIFIC/PREFERRED EMBODIMENTS OF THE INVENTION

More particularly according to the present invention, the extracts employed are extracts of at least one plant from the genus Saxifraga, as described by G. Bonnier in *La Grande Flore* from Gaston Bonnier Editions Belin, Nov. 1990, Institut National de la Recherche Agronomique & Delachaux & Nestlé S. A. The invention thus relates to plants of the genus Saxifraga as described by G. Bonnier.

The plants of the genus Saxifraga are known on the one hand as ornamental plants, but also for phytotherapy applications because of their aperitive, astringent, cholagogic and/or diuretic properties.

However, their use as skin-coloring agents as described above was hitherto unknown.

The plants of the genus Saxifraga belong to the family of Saxifragacea and the genus comprises about 630 species, among which are, for example and without limitation, *Saxifraga cuneifolia, Saxifraga glaucescens, Saxifraga rotundifolia, Saxifraga granulata, Saxifraga bulbifera, Saxifraga umbrosa* and *Saxifraga tridactylites*.

The extract of at least one plant from the genus Saxifraga according to the invention is advantageously an extract of a plant from a species selected from among *Saxifraga cuneifolia, Saxifraga glaucescens, Saxifraga rotundifolia, Saxifraga granulata, Saxifraga bulbifera, Saxifraga umbrosa* and *Saxifraga tridactylites*.

In a preferred embodiment of the invention, the extract of at least one plant from the genus Saxifraga is an extract of a plant from a species selected from among *Saxifraga glaucescens, Saxifraga rotundifolia* and *Saxifraga granulata*.

The extract of at least one plant from the genus Saxifraga according to the invention can be recovered from plant material derived from the whole plant or from a plant part such as the leaves, stems, flowers, petals or roots, or alternatively from undifferentiated cells thereof.

By the expression "undifferentiated plant cells" is intended any plant cell which exhibits none of the characteristics of a specific specialization and which is capable of living by itself and independently of other cells.

According to the invention, the whole or entire plant is preferably employed, particularly the stem and/or the leaves and most preferably the leaves.

The extract of at least one plant from the genus Saxifraga can be any extract prepared from any plant material derived from at least one plant from the genus Saxifraga cultivated in vivo or obtained from in vitro culturing.

By the expression "in vivo culturing" is intended any culturing of conventional type, i.e., in soil in the open air or in a greenhouse, or alternatively without soil.

By the expression "in vitro culturing" is intended the set of techniques known to this art which makes it possible to artificially obtain a plant or a part of a plant. The pressure of selection imposed by the physicochemical conditions during the growth of the plant cells in vitro produces a standardized plant material which is available throughout the year, unlike plants cultivated in vivo.

According to the invention, a plant of the genus Saxifraga obtained via in vitro culturing is preferably employed.

Any extraction technique known to this art can be used to separate the extract according to the invention.

Particularly exemplary are alcoholic extracts, in particular ethanolic extracts, or aqueous/alcoholic extracts.

The extract is preferably an aqueous extract.

An extract prepared via the technique described in FR-95/02379, assigned to the assignee hereof, can also be used.

Thus, in a first step, the plant material is ground in an aqueous solution under cold conditions, and, in a second step, the particles in suspension are removed from the aqueous solution obtained in the first step. This aqueous solution corresponds to the extract.

The aqueous solution obtained from the second step is optionally sterilized in a third step.

This extract can then be lyophilized.

The first step can be advantageously replaced with an operation of simple freezing of the plant tissues (for example at −20° C. or at −180° C. in liquid nitrogen), followed by aqueous extraction repeating the second and third steps described above.

The cold-temperature treatment allows the enzymatic activities to be frozen, and the sterilizing filtration avoids the degradation of the active agents by environmental microorganisms. Finally, the water vehicle is compatible with the ex vivo receptors and facilitates cosmetic or pharmaceutical formulations.

It is known that plant extracts contain oxidases that are responsible, inter alia, for the oxidation of said extracts. In point of fact, such oxidation imparts to the extracts a dark brown coloration and an acrid odor, thus making them unsuitable for formulation into cosmetics. Similarly, a lactase whose molecular weight is greater than 100,000 daltons is known, in particular.

Thus, the extract obtained can be advantageously fractionated by any known fractionation technique for removing oxidases, and in particular polyphenol oxidase. For example, the extract of the invention can be filtered through a dialysis membrane in order to remove the molecules whose molecular weight is greater than 100,000 daltons. It is also possible to subject the extract to a fractionation by selective precipitations.

Other methods make it possible to protect against oxidation phenomena. In particular, the extract can also be stabilized. Any known stabilization method can be used according to the invention. For example, the extract of the invention can be stabilized by bubbling nitrogen therethrough in order to remove the dissolved oxygen, or alternatively by adding cysteine and/or sulfur derivatives thereto to a final concentration ranging from 0.5 g/l to 10 g/l and preferably from 1 g/l to 2.5 g/l.

It will of course be appreciated that the extract according to the invention can be fractionated and stabilized.

The extract can itself constitute the active principle of the compositions of the invention.

One embodiment of a preparation of an extract which can be employed according to the invention is given in the examples which follow.

The extract of at least one plant from the genus Saxifraga is preferably present in the compositions according to the invention in proportions that are sufficient to impart to the skin, after application, a coloration similar to the coloration obtained after natural tanning. It is thus generally present in proportions of ranging from 0.05% to 20% by weight relative to the total weight of the composition, and preferably from 0.5% to 10% by weight relative to the total weight of the composition.

It will also be appreciated that the compositions of the present invention can contain one or more other skin-coloring agents such as, for example, mono- or polycarbonyl compounds such as isatin, alloxan, ninhydrin, glyceraldehyde, mesotartaric aldehyde, or pyrazoline-4,5-dione compounds, and these skin-coloring agents may be combined with direct dyes or indole derivatives.

In one preferred embodiment of the invention, the compositions also comprise dihydroxyacetone (DHA).

Thus, the present invention also features compositions which comprise, formulated into a physiologically acceptable support, an extract of at least one plant from the genus Saxifraga as described above and at least one other skin-coloring agent. According to the invention, such other skin-coloring agent is preferably selected from among mono- or polycarbonyl compounds such as isatin, alloxan, ninhydrin, glyceraldehyde, mesotartaric aldehyde, pyrazoline-4,5-dione compounds and dihydroxyacetone.

The other skin-coloring agent is very preferably dihydroxyacetone (DHA).

Specifically, dihydroxyacetone and the extracts of at least one plant from the genus Saxifraga described above exhibit excellent chemical compatibility in compositions comprised thereof, as well as very good complementarity of the colorations they impart to the skin. This makes it possible, by combining these in suitable proportions, to achieve an artificial skin coloration that is remarkably close to the coloration imparted by natural tanning.

The other skin-coloring agent is advantageously present in the compositions according to the invention in proportions which allow the combination of the two skin-coloring agents to impart to the skin, after application, a coloration which is as close as possible to that provided by natural tanning. The skin-coloring agent is thus generally present in an amount by weight ranging from 0.5% to 10% relative to the total weight of the composition, and preferably from 1% to 7% by weight relative to the total weight of the composition.

The dihydroxyacetone can also be applied to the skin in the form of an independent composition, separately of the composition comprising the extract of at least one plant from the genus Saxifraga, for example before or after applying the latter composition.

In another preferred embodiment of the cosmetic regime/regimen according to the invention, a composition comprising dihydroxyacetone is topically applied in a first stage, and the composition comprising the extract of at least one plant from the genus Saxifraga is then topically applied in a second stage, in order, at the user's discretion, to modify the shade of the coloration provided by dihydroxyacetone alone, which is occasionally considered as being slightly too yellow.

The compositions according to the invention can also contain one or more hydrophilic or lipophilic sunscreens that are active in the UVA and/or UVB range, or, alternatively, coated or uncoated metal oxide pigments.

The compositions according to the invention can be cosmetic or dermatological compositions. Consistent herewith, the compositions are preferably cosmetic formulations.

The compositions of this invention can also comprise conventional adjuvants and additives selected, in particular, from among fatty substances, organic solvents, ionic or nonionic thickeners, softeners, antioxidants, free-radical scavengers, opacifiers, stabilizers, emollients, silicones, α-hydroxy acids, antifoaming agents, moisturizers, vitamins, fragrances, preservatives, surfactants, fillers, sequestering agents, polymers, propellants, acidifying or basifying agents, dyes, colorants, or any other ingredient conventional in this field, in particular for the formulation of antisun/sunscreen compositions as emulsions.

The fatty substances are advantageously oils or waxes or mixtures thereof. By the term "oil" is intended a compound which is liquid at room temperature. By the term "wax" is intended a compound which is solid or substantially solid at room temperature, and whose melting point is generally greater than 35° C.

Exemplary oils are mineral oils (petroleum jelly); plant oils (sweet almond oil, macadamia oil, blackcurrant seed oil or jojoba oil); synthetic oils such as perhydrosqualene, fatty alcohols, fatty acids or fatty esters (such as the C12–C15 alkyl benzoate marketed under the trademark "Finsolv TN" by Finetex, octyl palmitate, isopropyl lanolate, triglycerides including those of capric/caprylic acids), oxyethylenated or oxypropylenated fatty esters and fatty ethers; silicone oils (cyclomethicone, polydimethylsiloxanes or PDMSs) or fluoro oils, and polyalkylenes.

Exemplary waxy compounds are paraffin, carnauba wax, beeswax and hydrogenated castor oil.

Exemplary organic solvents are the lower alcohols and polyols.

And exemplary thickeners include, in particular, crosslinked polyacrylic acids and modified or unmodified guar gums and celluloses, such as hydroxypropyl guar gum, methylhydroxyethylcellulose and hydroxypropylmethylcellulose.

One skilled in this art will of course take care to select the optional additional compound(s) indicated above and/or the amounts thereof such that the advantageous properties intrinsically associated with the use of at least one extract of at least one plant from the genus Saxifraga in accordance with the invention are not, or are not substantially, adversely affected by the addition(s) envisaged.

The compositions according to the invention can be formulated according to the techniques that are well known to those skilled in the art, in particular those suitable for the formulation of emulsions of oil-in-water (O/W) or water-in-oil (W/O) type.

Such a composition can be, in particular, in the form of a simple or complex emulsion (O/W, W/O, O/W/O or W/O/W emulsion) such as a cream or a milk, or in the form of a gel or a cream/gel, in the form of a lotion, an ointment, a powder or a solid tube or stick, and can optionally be packaged as an aerosol and can be in the form of a mousse or a spray.

The compositions according to the invention are preferably oil-in-water emulsions.

When the composition is an emulsion, the aqueous phase of this composition can comprise a nonionic vesicular dispersion formulated according to known processes (Bangham, Standish and Watkins, *J. Mol. Biol.*, 13, 238 (1965), FR-2,315,991 and FR-2,416,008).

In order to further illustrate the present invention and the advantages thereof, the following specific examples are given, it being understood that same are intended only as illustrative and in nowise limitative.

EXAMPLE 1

Preparation of an Extract of *Saxifraga granulata*

500 grams of *Saxifraga granulata* plant material, above ground part corresponding to stems and leaves, were immersed in about 1 kg of liquid nitrogen.

After removing the stems, the leaves were reduced to powder by grinding with a Turrax machine at 24,000 rpm for 1 minute at 4° C. (ice bath).

The powder obtained was mixed with 5 liters of 0.05 M phosphate buffer at pH 8.5. The mass was stirred for 30 minutes at 4° C. and then centrifuged at 10,000×G at 4° C. The supernatant was filtered through a 0.22 $\mu$m filter (sterilizing filtration).

The extract was then fractionated by ultrafiltration through a membrane of Sartorius type in order to eliminate the oxidation phenomena.

The extract was then lyophilized. About 5 grams of active extract referred to as "lyophilized extract" were thus obtained.

EXAMPLE 2

In Vitro Test of Skin Coloration 5 grams of fresh leaves of *Saxifraga granulata* were chopped up using a scalpel and then rubbed on an artificial skin equivalent such as the vitro-skin marketed by the IMS testing group, of surface area 8.41 $cm^2$, which had been prehydrated for 24 hours in a hermetically sealed chamber containing a water/glycerol mixture (70/30).

A heterogeneous orange coloration was observed.

The color of the skin was evaluated before and after dyeing, in the L a b system, using a Minolta chromameter (model CR200). In the Lab system, the three parameters respectively denote the intensity (L), the shade (a) and the saturation (b).

According to this system, the higher the value of L, the paler or less intense the color. Conversely, the lower the value of L, the darker or more intense the color.

a and b indicate two color axes, a indicating the green/red color axis and b indicating the blue/yellow axis. Values close to zero for a and b correspond to grey shades.

The coloration (ΔE) can be calculated according to the following equation:

$$\Delta E = \sqrt{(\Delta L)^2 + (\Delta a)^2 + (\Delta b)^2}$$

in which:

$\Delta L = L - L_o$, $\Delta a = a - a_o$ and $\Delta b = b - b_o$, L, a and b respectively representing the intensity, the shade and the saturation of the skin after coloration, $L_o$, $a_o$ and $b_o$ respectively representing the intensity, the shade and the saturation of the skin before coloration.

The higher the value of ΔE, the greater the difference in color between the uncolored skin and the colored skin.

The following values were observed:

| ΔL | Δa | Δb | ΔE |
|---|---|---|---|
| −12.90 | −2.50 | 15.70 | 20.47 |

These results confirm the capacity of *Saxifraga granulata* to color the skin in orange tones.

EXAMPLE 3

The following are specific examples of formulations according to the invention and particularly are compositions combining at least one extract of at least one plant from the genus Saxifraga and DHA.

These compositions were formulated by simple mixing of the various constituents thereof.

| Composition A: | |
|---|---|
| Montanov 68 ®* | 7.5% |
| Dimethicone | 0.5% |
| Finsolv TN ®** | 15.0% |
| Propylene glycol | 10.0% |
| Dihydroxyacetone | 5.0% |
| Extract of *Saxifraga granulata* | 5.0% |
| Preservatives | q.s. |
| Water | q.s. |
| 100.0% | |
| Composition B: | |
| Extract of *Saxifraga granulata* | 7.0% |
| Ceteareth 30 | 7.0% |
| Glyceryl stearate | 2.0% |
| Cetyl alcohol | 1.5% |
| Polydimethylsiloxane | 1.5% |
| Liquid paraffin | 15.0% |
| Pure glycerol codex | 20.0% |
| Demineralized water q.s. | 100.0% |
| Preservatives | q.s. |

| -continued | |
|---|---|
| Composition C: | |
| Extract of *Saxifraga granulata* | 15.0% |
| Dihydroxyacetone | 1.0% |
| Ethanol | 30.0% |
| Demineralized water q.s. | 100.0% |

*Cetylstearyl glucoside/cetystearyl alcohol mixture marketed by SEPPIC
**C12–C15 alkyl benzoate marketed by Finetex While the invention has been described in terms of various specific and/or preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime/regimen for the artificial tanning/coloration of human skin, comprising topically applying thereto, for such period of time as required to elicit the desired response, an effective self-tanning/coloring amount of at least one extract of at least one plant of the genus Saxifraga.

2. The regime/regimen as defined by claim 1, said at least one plant of the genus Saxifraga comprising a species *Saxifraga cuneifolia, Saxifraga glaucescens, Saxifraga rotundifolia, Saxifraga granulata, Saxifraga bulbifera, Saxifraga umbrosa* or *Saxifraga tridactylites*.

3. The regime/regimen as defined by claim 2, said at least one plant of the genus Saxifraga comprising a species *Saxifraga glaucescens, Saxifraga rotundifolia* or *Saxifraga granulata*.

4. The regime/regimen as defined by claim 1, said at least one extract having been separated from the whole plant of the genus Saxifraga, or from a Saxifraga plant part.

5. The regime/regimen as defined by claim 4, said at least one extract having been separated from the leaves, stems, flowers, petals, roots and/or undifferentiated cells of said at least one plant of the genus Saxifraga.

6. The regime/regimen as defined by claim 5, said at least one extract having been separated from the leaves of said at least one plant of the genus Saxifraga.

7. The regime/regimen as defined by claim 1, said at least one plant of the genus Saxifraga having been cultivated in vivo or obtained via in vitro culturing.

8. The regime/regimen as defined by claim 7, said at least one plant of the genus Saxifraga having been cultivated in vitro.

9. The regime/regimen as defined by claim 1, said at least one extract comprising an aqueous extract.

10. The regime/regimen as defined by claim 1, further comprising topically co-applying to said human skin, also for such period of time as required to elicit the desired response, an effective self-tanning/coloring amount of at least one other artificial tanning agent other than said at least one extract of at least one plant of the genus Saxifraga.

11. The regime/regimen as defined by claim 10, said at least one other artificial tanning agent comprising a mono- or polycarbonyl compound, isatin, alloxan, ninhydrin, glyceraldehyde, mesotartaric aldehyde, a pyrazoline-4,5-dione compound, and/or dihydroxyacetone.

12. The regime/regimen as defined by claim 11, said at least one other artificial tanning agent comprising dihydroxyacetone.

13. A topically applicable cosmetic/dermatological composition adopted for the artificial tanning/coloration of human skin, comprising an effective self-tanning/coloring amount of at least one extract of at least one plant of the genus *Saxifraga*, formulated into a topically applicable, physiologically/cosmetically acceptable vehicle, diluent or carrier therefor.

14. The topically applicable cosmetic/dermatological composition as defined by claim 13, further comprising an effective self-tanning/coloring amount of at least one other artificial tanning agent other than said at least one extract of at least one plant of the genus Saxifraga.

15. The topically applicable cosmetic/dermatological composition as defined by claim 13, comprising from 0.5% to 10% by weight of said at least one extract of at least one plant of the genus Saxifraga.

16. The topically applicable cosmetic/dermatological composition as defined by claim 16, comprising from 1% to 7% by weight of said at least one extract of at least one plant of the genus Saxifraga.

17. The topically applicable cosmetic/dermatological composition as defined by claim 14, said at least one plant of the genus Saxifraga comprising a species *Saxifraga cuneifolia, Saxifraga glaucescens, Saxifraga rotundifolia, Saxifraga granulata, Saxifraga bulbifera, Saxifraga umbrosa* or *Saxifraga tridactylites*.

18. A regime/regimen for the artificial tanning/coloration of human skin, comprising topically applying an effective self-tanning/coloring amount of dihydroxyacetone thereto, and then topically applying thereto an effective self-tanning/coloring amount of at least one other artificial tanning agent comprising at least one extract of at least one plant of the genus *Saxifraga*.

19. The topically applicable cosmetic/dermatological composition as defined by claim 13, further comprising a fatty substance, organic solvent, ionic or nonionic thickener, softener, antioxidant, free-radical scavenger, opacifier, sunscreen, stabilizer, emollient, silicone, α-hydroxy acid, antifoaming agent, moisturizer, vitamin, fragrance, preservative, surfactant, filler, sequestering agent, polymer, propellant, acidifying or basifying agent, dye, colorant, or combination thereof.

20. The topically applicable cosmetic/dermatological composition as defined by claim 13, comprising an emulsion, cream, gel, milk, cream/gel, lotion, ointment, powder, solid tube or stick, mousse, spray, or nonionic vesicular dispersion.

21. The regime/regimen as defined by claim 1, said at least one extract of at least one plant of the genus Saxifraga being reduced in oxidase values.

22. The topically applicable cosmetic/dermatological composition as defined by claim 13, said at least one extract of at least one plant of the genus Saxifraga being reduced in oxidase values.

23. The topically applicable cosmetic/dermatological composition as defined by claim 14, said at least one extract of at least one plant of the genus Saxifraga being reduced in oxidase values.

* * * * *